(12) United States Patent
Lee et al.

(10) Patent No.: US 8,502,165 B2
(45) Date of Patent: Aug. 6, 2013

(54) ULTRAVIOLET STERILIZER HAVING WATERTIGHT FUNCTION

(75) Inventors: Soo-Tae Lee, Busan (KR); Tae-Sung Pyo, Busan (KR); Su-Kyu Lee, Busan (KR)

(73) Assignee: Panasia Co., Ltd., Busan (KR)

( * ) Notice: Subject to any disclaimer, the term of this patent is extended or adjusted under 35 U.S.C. 154(b) by 96 days.

(21) Appl. No.: 13/000,998

(22) PCT Filed: Jun. 18, 2010

(86) PCT No.: PCT/KR2010/003970
§ 371 (c)(1),
(2), (4) Date: Dec. 22, 2010

(87) PCT Pub. No.: WO2011/155656
PCT Pub. Date: Dec. 15, 2011

(65) Prior Publication Data
US 2012/0248330 A1   Oct. 4, 2012

(30) Foreign Application Priority Data
Jun. 11, 2010 (KR) .................. 10-2010-0055639

(51) Int. Cl.
*G01N 23/00* (2006.01)

(52) U.S. Cl.
USPC ............ 250/455.11; 250/453.11; 250/454.11; 250/504 R; 250/432 R (58) Field of Classification Search
None
See application file for complete search history.

(56) References Cited

U.S. PATENT DOCUMENTS

| 5,471,063 | A | | 11/1995 | Hayes et al. |
| 5,765,403 | A | * | 6/1998 | Lincoln et al. ................ 68/13 R |
| 5,993,749 | A | * | 11/1999 | Adams ....................... 422/186.3 |
| 6,039,460 | A | * | 3/2000 | Ng et al. ....................... 362/267 |
| 6,048,219 | A | * | 4/2000 | Kotowski ..................... 439/221 |
| 6,296,775 | B1 | * | 10/2001 | Moody et al. ............ 210/748.11 |
| 6,614,039 | B2 | * | 9/2003 | Hollander ................. 250/504 R |
| 2004/0025899 | A1 | * | 2/2004 | Pinsky ......................... 132/310 |
| 2004/0134861 | A1 | * | 7/2004 | Brodie ......................... 210/748 |
| 2004/0195954 | A1 | * | 10/2004 | Pirovic ......................... 313/490 |
| 2006/0163168 | A1 | * | 7/2006 | Moody et al. ................ 210/748 |
| 2006/0263075 | A1 | * | 11/2006 | Juan et al. ....................... 396/29 |
| 2006/0267495 | A1 | * | 11/2006 | Pirovic ......................... 313/547 |
| 2007/0241288 | A1 | | 10/2007 | Wang |
| 2008/0210884 | A1 | * | 9/2008 | Egberts ........................ 250/429 |
| 2008/0265775 | A1 | | 10/2008 | Schiene et al. |
| 2010/0300982 | A1 | * | 12/2010 | Nilsen ..................... 210/748.11 |

FOREIGN PATENT DOCUMENTS

| KR | 20-0376626 | 3/2005 |
| KR | 20-0435974 | 3/2007 |
| WO | WO 95/19188 | 7/1995 |

* cited by examiner

*Primary Examiner* — Andrew Smyth
(74) *Attorney, Agent, or Firm* — Rabin & Berdo, P.C.

(57) ABSTRACT

Disclosed herein is an ultraviolet sterilizer having a watertight function. The ultraviolet sterilizer includes a housing and an ultraviolet sterilization unit. The housing has an inlet through which ballast water is drawn into the housing, and an outlet through which the ballast water is discharged from the housing after the ballast water has been sterilized. The ultraviolet sterilization unit is provided in the housing and includes an ultraviolet lamp applying ultraviolet rays to the ballast water to sterilize the ballast water. The ultraviolet sterilizer further includes a cap which supports each of the opposite ends of the ultraviolet sterilization unit and is watertightly coupled to the housing. Thus, even if the ultraviolet sterilization unit is damaged, ballast water is prevented from being drawn into a reception space which contains external devices, and explosive gas which may cause the ultraviolet sterilizer to explode is also prevented from entering the cap.

1 Claim, 12 Drawing Sheets

Figure 12 ically, to an ultraviolet sterilizer including: a housing which has an inlet through which ballast water is drawn into the housing, and an outlet through which the ballast water is discharged from the housing after the ballast water has been sterilized; and an ultraviolet sterilization unit which is provided in the housing and includes an ultraviolet lamp applying ultraviolet rays to the ballast water to sterilize the ballast water, wherein the ultraviolet sterilizer further includes a cap which supports each of the opposite ends of the ultraviolet sterilization unit, the cap in watertight contact with the housing, so that if the ultraviolet sterilization unit is damaged, ballast water is prevented from being drawn into a reception space which contains external devices disposed outside the cap, and explosive gas which may cause the ultraviolet sterilizer to explode is also prevented from entering the cap.

2. Description of the Related Art

Generally, when cargo ships sail with no cargo, ballast water is loaded in tanks of the cargo ships to keep the ships in balance. However, unfortunately, ballast water used in the cargo ships may damage native marine ecosystems because of the foreign marine creatures which have been contained in the ballast water. Therefore, it is required to treat the ballast water. To date, methods of applying ultraviolet rays to ballast water have been widely used.

Figure 1:
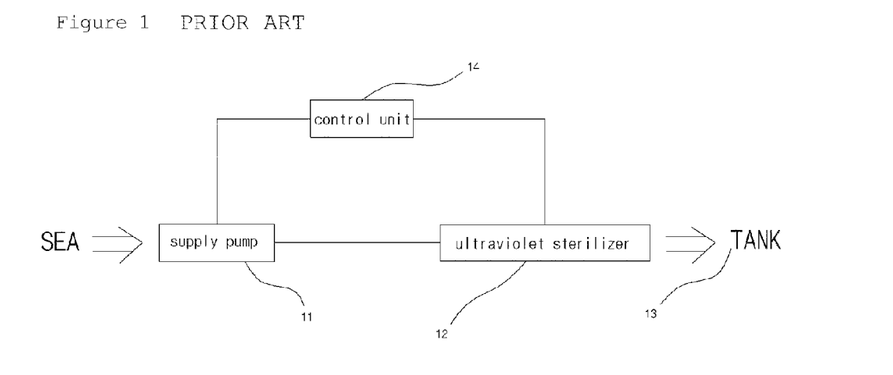
FIG. 1 is a block diagram of a conventional ballast water treatment system.
Figure 2:
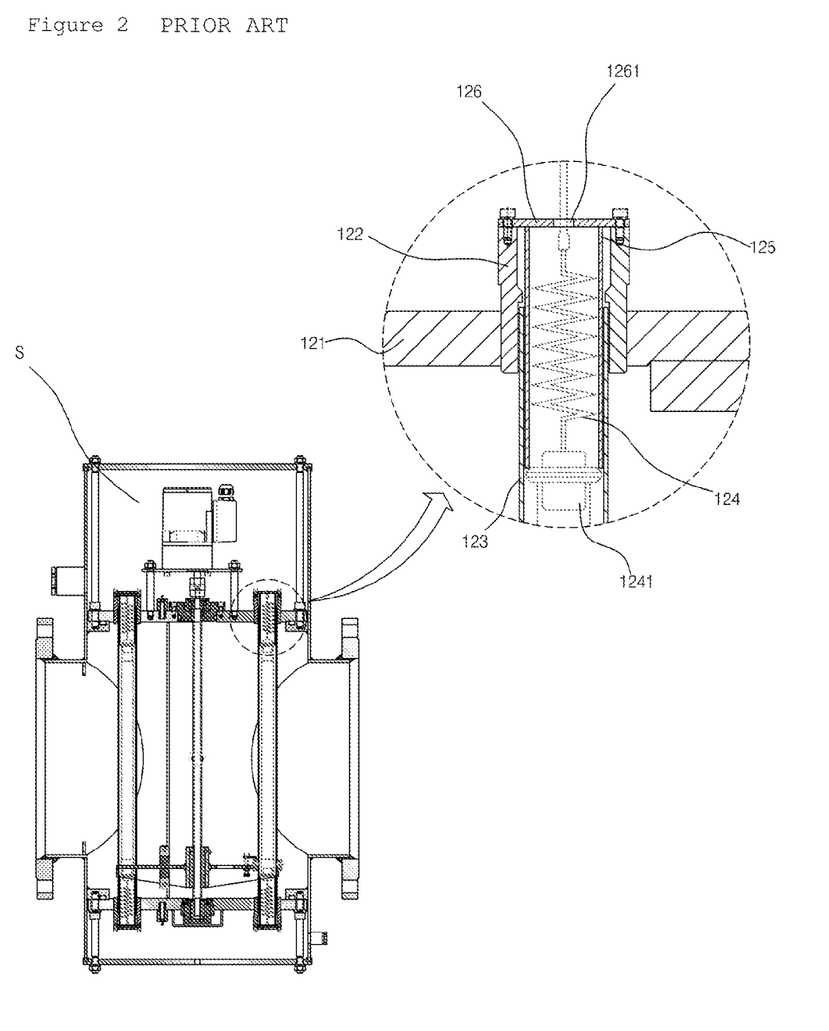
FIG. 2 is a sectional view showing an ultraviolet sterilizer of the conventional ballast water treatment system.

FIG. 1 is a block diagram of a conventional ballast water treatment system. FIG. 2 is a sectional view showing an ultraviolet sterilizer of the conventional ballast water treatment system. In the conventional ballast water treatment system, a supply pump 11 supplies ballast water to an ultraviolet sterilizer 12, and the ultraviolet sterilizer 12 sterilizes the ballast water and discharges it into a tank 13. A control unit 14 controls the entirety of the system.

In the conventional ultraviolet sterilizer 12, a through hole is formed through a housing cover 121 to facilitate replacement of a sleeve pipe 123 and an ultraviolet lamp 1241. A cap 122 having a cylindrical shape which is open on upper and lower ends thereof is removably coupled to the through hole of the housing cover 121. The cap 122 supports the sleeve pipe 123. The ultraviolet lamp 1241 is disposed in the sleeve pipe 123 and supported by a support 125. Furthermore, a cap cover 126 is removably coupled to an upper end of the cap 122 by screws or the like. A passing hole 1261 is formed through the cap cover 126 so that a lead wire 124 of the ultraviolet lamp 1241 is led out of the cap 122 through the passing hole 1261.

However, the sleeve pipe 123 or the ultraviolet lamp 1241 may be damaged on accident or by impurities drawn into the ultraviolet sterilizer during the process of sterilizing ballast water. In this case, ballast water which has been in the ultraviolet sterilizer may leak out of the cap through the junction between the cap 122 and the cap cover 126 or the passing hole 1261 of the cap cover 126 and enter a reception space S which contains several devices for operating the ultraviolet sterilizer. Such leaking may damage the devices of the ultraviolet sterilizer.

Moreover, several devices or machines are present around the ultraviolet sterilizer. Particularly, explosive gas may be present around the ultraviolet sterilizer. If explosive gas enters the cap 122, the ultraviolet sterilizer may be exploded by a spark.

SUMMARY OF THE INVENTION

Accordingly, the present invention has been made keeping in mind the above problems occurring in the prior art, and an object of the present invention is to provide an ultraviolet sterilizer having a watertight function which includes a cap which is coupled in a watertight manner to a housing, so that even if the ultraviolet sterilization unit is damaged and ballast water is drawn into the cap, the ballast water can be prevented from entering a reception space which is formed outside the cap and contains several devices belonging to the sterilizer.

Another object of the present invention is to provide an ultraviolet sterilizer in which power is supplied to an ultraviolet lamp through a conductor, so that a separate passing hole through which a lead wire of the ultraviolet lamp is led out of the cap is not required, thus further improving the watertight function.

A further object of the present invention is to provide an ultraviolet sterilizer in which an insulator covers the conductor to prevent electric current from being applied to parts other than the ultraviolet lamp.

A still further object of the present invention is to provide an ultraviolet sterilizer in which a sealing member is interposed between an upper surface of a cap body and a lower surface of a cap cover, and a pressure controller includes a backflow prevention valve, so that the control of the internal pressure of the cap and opening of the cap can be facilitated by the improved watertight function.

A still further object of the present invention is to provide an ultraviolet sterilizer which includes the pressure controller which supplies air into the cap to maintain the internal pressure of the cap higher than the external pressure, so that explosive gas can be prevented from entering the cap, thus preventing the explosive gas from causing the ultraviolet sterilizer to explode.

A still further object of the present invention is to provide an ultraviolet sterilizer which may include a shock absorption unit which absorbs vibrations of the ultraviolet lamp, thus protecting the sleeve pipe or the ultraviolet lamp from being damaged.

A still further object of the present invention is to provide an ultraviolet sterilizer in which an upper body of the cap is removably coupled by screwing to a lower body of the cap such that only the upper body of the cap is separated from the ultraviolet sterilizer, so that a through hole to which the cap is coupled can be opened while the ultraviolet sterilization unit is still fastened to the housing of the ultraviolet sterilizer and, thus, some parts of the ultraviolet sterilization unit can be easily replaced with new ones without removing the entirety of the ultraviolet sterilization unit.

In order to accomplish the above object, the present invention provides an ultraviolet sterilizer having a watertight function, including: a housing having an inlet through which ballast water is drawn into the housing, and an outlet through which the ballast water is discharged from the housing after the ballast water has been sterilized; an ultraviolet sterilization unit provided in the housing, the ultraviolet sterilization unit comprising an ultraviolet lamp applying ultraviolet rays to the ballast water to sterilize the ballast water; and a cap supporting each of opposite ends of the ultraviolet sterilization unit, the cap being watertightly coupled to the housing, so that when the ultraviolet sterilization unit is damaged, ballast water is prevented from being drawn into a reception space, containing external devices located outside the cap.

The cap may include a conductor connected to the ultraviolet lamp to supply power to the ultraviolet lamp, the conductor being made of electric conductive material; and an insulator covering an outer surface of the conductor, the insulator being made of insulation material.

The conductor may include a conductor body forming an external shape of the conductor; and upper and lower wire connectors respectively protruding from upper and lower ends of the conductor body. The lower wire connector may be disposed inside the cap and connected to a lead wire of the ultraviolet lamp, and the upper wire connector may be located outside the cap and connected to a power supply, the power supply supplying power to the ultraviolet lamp.

Furthermore, each of the wire connectors may comprise an external thread formed on an outer circumferential surface thereof, and a nut threaded over the external thread, so that a process of connecting the lead wire to the wire connector is facilitated.

The ultraviolet sterilizer may further include a pressure controller connected to a predetermined portion of the cap, the pressure controller supplying air into the cap such that an internal pressure of the cap is maintained higher than an external pressure thereof.

The cap may have an air inlet hole formed through the predetermined portion of the cap, and the pressure controller may include: a connector coupled to the air inlet hole; an air supply tube connected at a first end thereof to the connector; and an air supply unit connected to a second end of the air supply tube, the air supply unit generating air pressure to supply air into the air supply tube.

The pressure controller may further include a backflow prevention valve provided at a predetermined position in the air supply tube to prevent ballast water from flowing backwards from the cap towards the air supply unit.

The cap may include a cap body coupled at a predetermined position to the housing, the cap body holding an end of a sleeve pipe and being open on opposite ends thereof; and a cap cover removably coupled to the cap body to cover an upper end of the cap body.

The cap may further include a sealing member interposed between the upper end of the cap body and a lower surface of the cap cover to provide a watertight seal between the cap body and the cap cover.

The cap cover may include a conductor connected to the ultraviolet lamp to supply power to the ultraviolet lamp, the conductor being made of electric conductive material; and an insulator covering an outer surface of the conductor, the insulator being made of insulation material.

The conductor may include a conductor body forming an external shape of the conductor; and upper and lower wire connectors respectively protruding from upper and lower ends of the conductor body. The lower wire connector may be disposed inside the cap body and connected to a lead wire of the ultraviolet lamp, and the upper wire connector may be located outside of the cap body and connected to a power supply, the power supply supplying power to the ultraviolet lamp.

As described above, the ultraviolet sterilizer of the present invention includes a cap which is watertightly coupled to a housing. Therefore, even if an ultraviolet sterilization unit is damaged and ballast water is drawn in through the cap, the ballast water can be prevented from entering a reception space which is formed outside the cap and contains several devices of the sterilizer.

Furthermore, power is supplied to an ultraviolet lamp through a conductor, so that a separate passing hole through which a lead wire of the ultraviolet lamp is led out of the cap is not required. Thus, the watertight performance of the sterilizer can be markedly enhanced.

In addition, an insulator covers the conductor to prevent electric current from being applied to parts other than the ultraviolet lamp.

Moreover, a sealing member is interposed between an upper surface of a cap body and a lower surface of a cap cover, and a pressure controller includes a backflow prevention valve. Hence, the control of the internal pressure of the cap and opening of the cap can be facilitated with the improved watertight function.

The pressure controller supplies air into the cap such that the internal pressure of the cap is maintained higher than the external pressure, so that explosive gas can be prevented from entering the cap, thus preventing the ultraviolet sterilizer from being exploded by the explosive gas.

Furthermore, the ultraviolet sterilizer may include a shock absorption unit which absorbs vibrations of the ultraviolet lamp, thus preventing the sleeve pipe or the ultraviolet lamp from being damaged.

In addition, an upper body of the cap is removably coupled to a lower body of the cap by screwing such that only the upper body of the cap is separated from the ultraviolet sterilizer. Therefore, a through hole to which the cap is coupled can be opened with the ultraviolet sterilization unit being fastened to the housing of the ultraviolet sterilizer. Thus, some parts of the ultraviolet sterilization unit can be easily replaced with new ones without removing the entirety of the ultraviolet sterilization unit.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, an ultraviolet sterilizer having the watertight function of the present invention will be described in detail with reference to the attached drawings. Reference now should be made to the drawings, in which the same reference numerals are used throughout the different drawings to designate the same or similar components. In the following description, when it was determined that a detailed description of the conventional function and conventional structure would confuse the gist of the present invention, such description may have been omitted.

Figure 3:
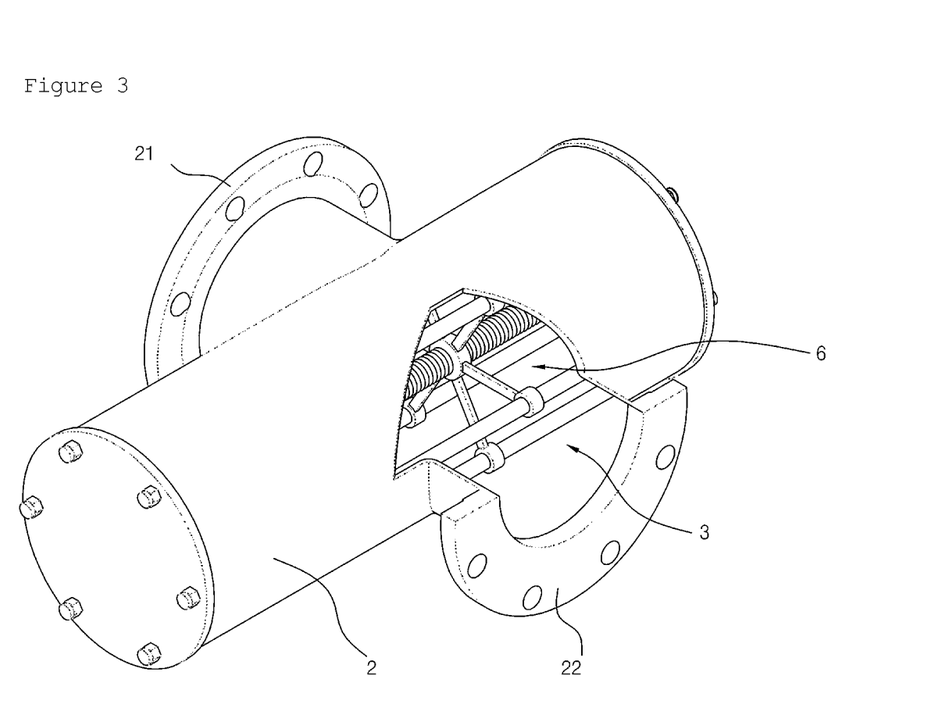
FIG. 3 is a partially broken perspective view of an ultraviolet sterilizer, according to a first embodiment of the present invention.
Figure 4:
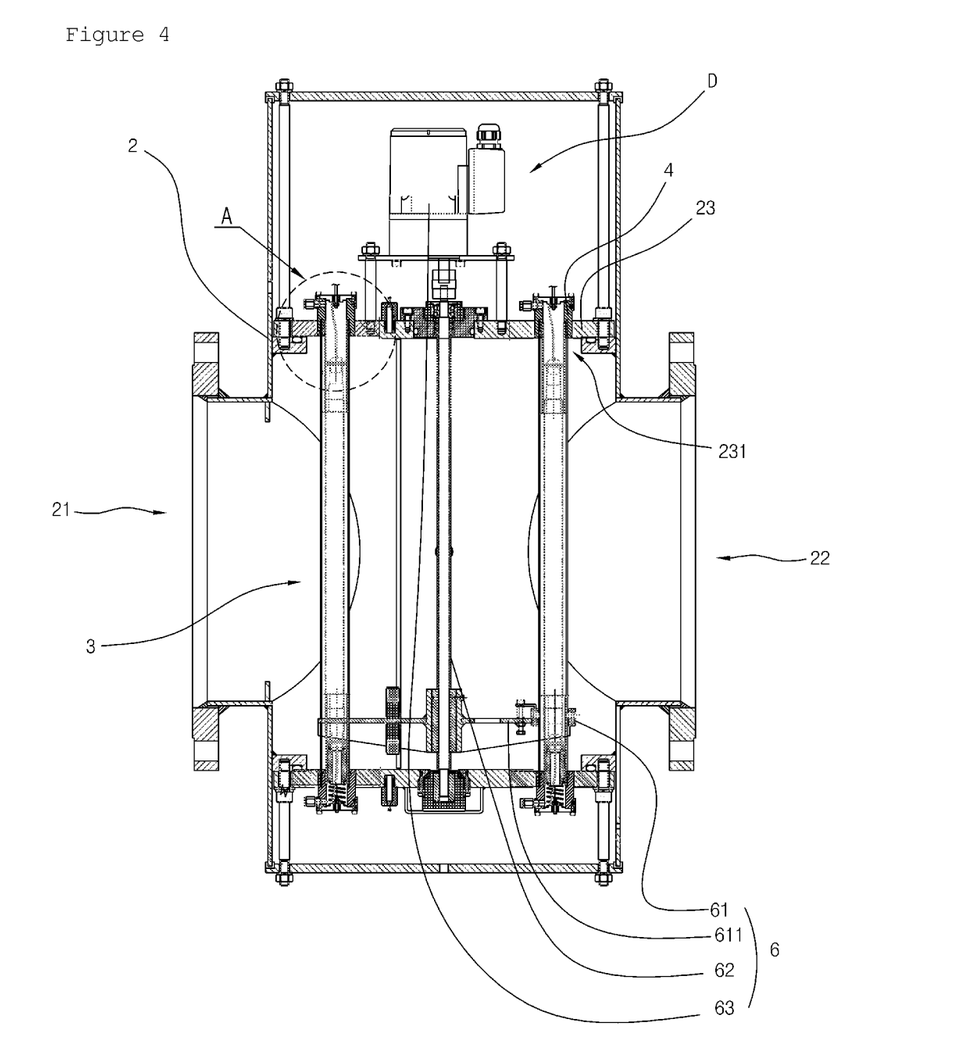
FIG. 4 is a sectional view showing the ultraviolet sterilizer according to the first embodiment of the present invention.
Figure 5:
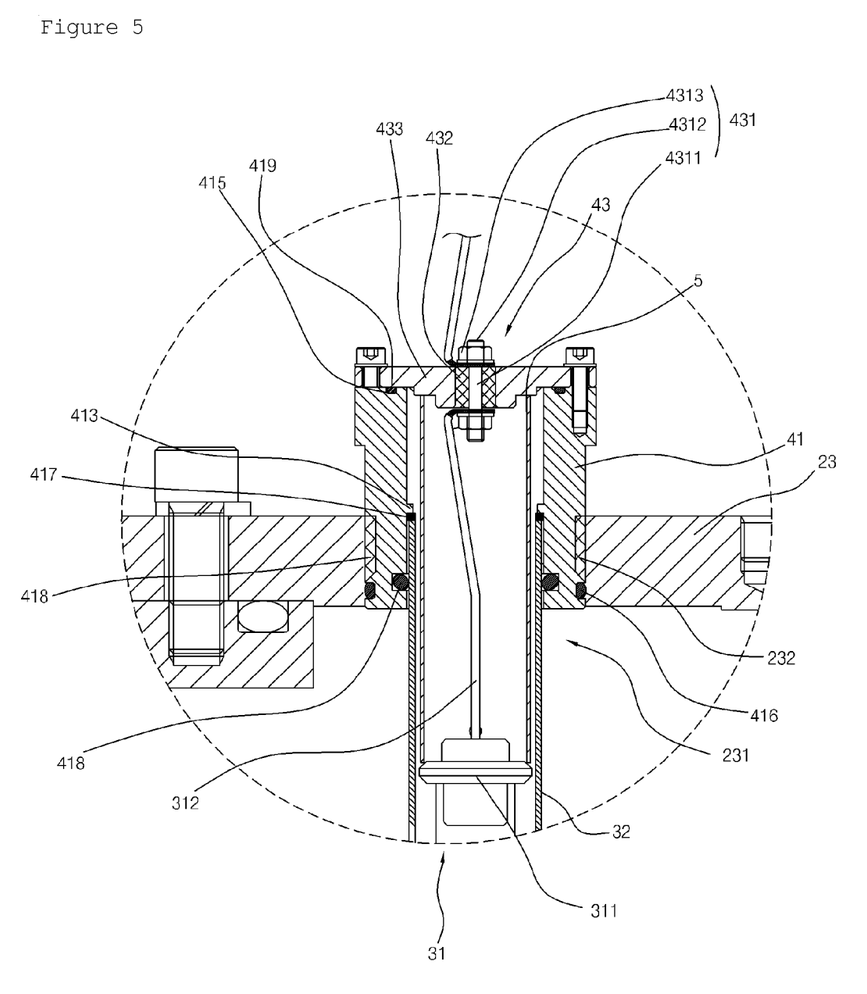
FIG. 5 is an enlarged view showing the circled portion A of FIG. 4 according to the first embodiment of the present invention.
Figure 6:
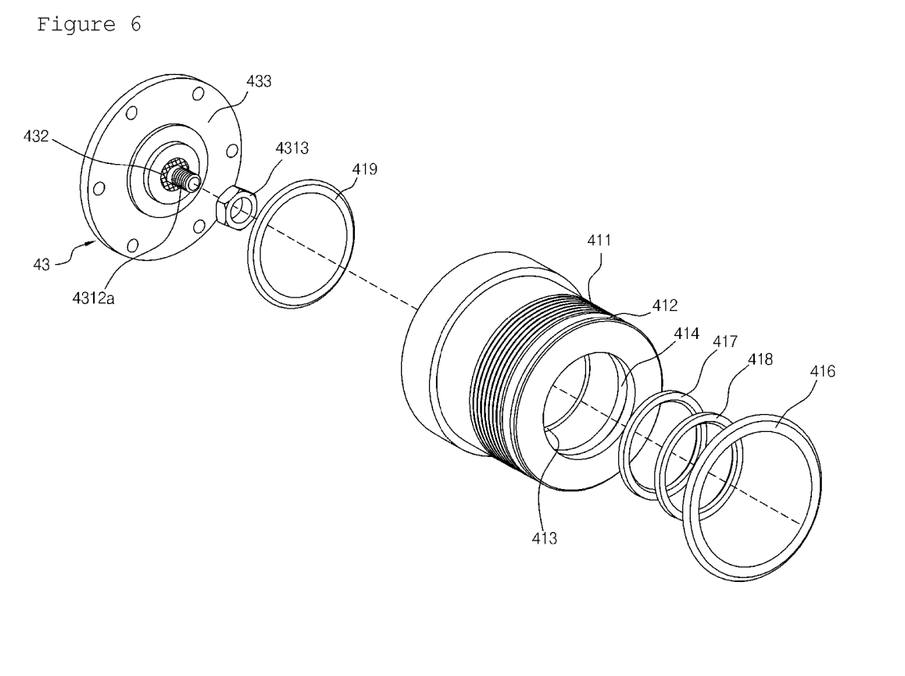
FIG. 6 is an exploded perspective view of a cap according to the first embodiment of the present invention.
Figure 7:
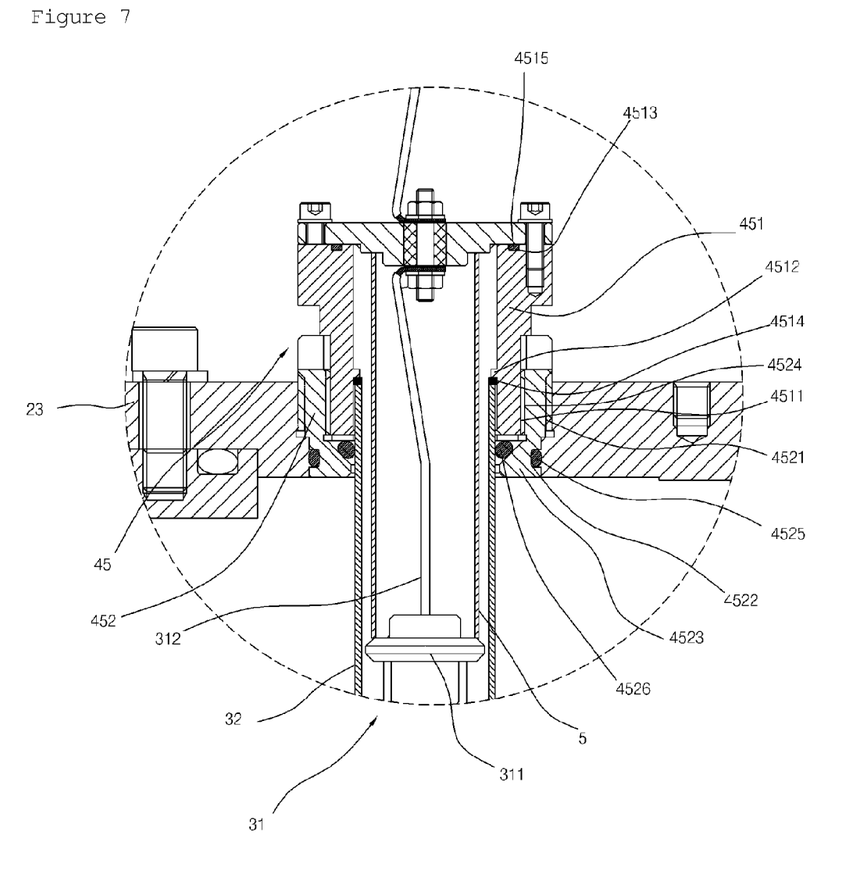
FIG. 7 is an enlarged view showing the circled portion A of FIG. 4 according to a second embodiment of the present invention.
Figure 8:
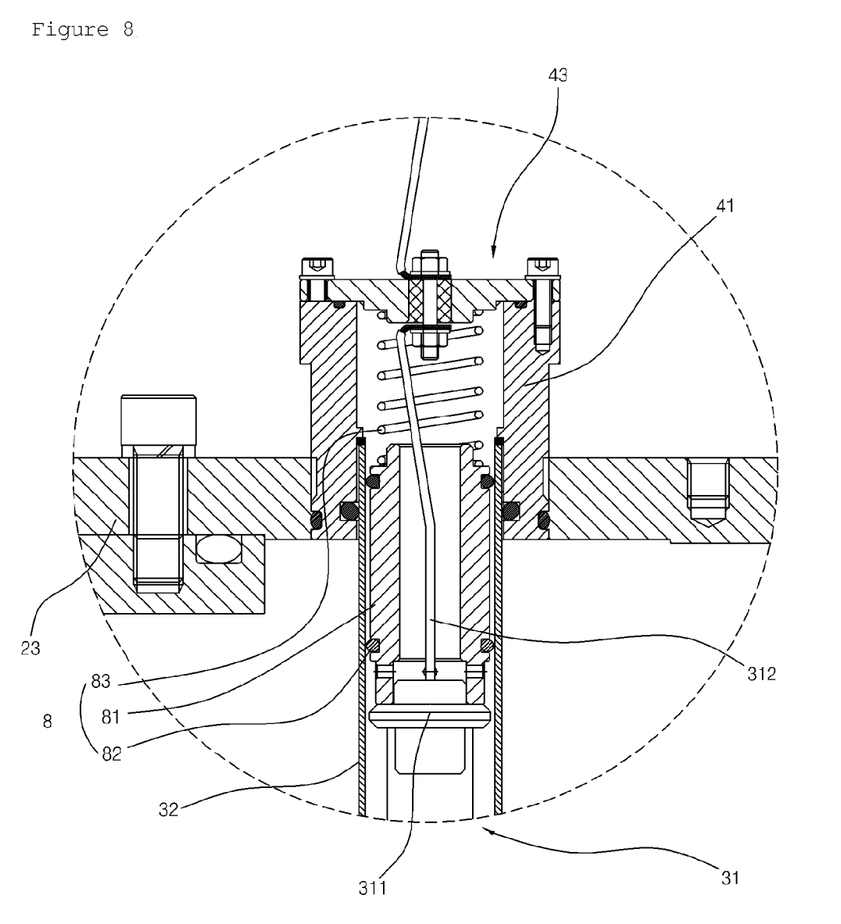
FIG. 8 is an enlarged view showing the circled portion A of FIG. 4 according to a third embodiment of the present invention.
Figure 9:
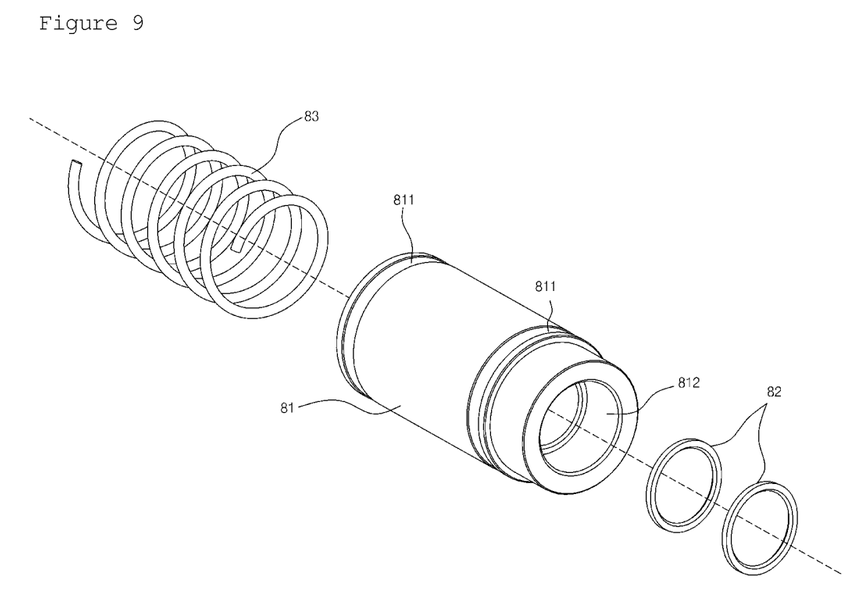
FIG. 9 is an exploded perspective view of a shock absorption unit according to the third embodiment of the present invention.
Figure 10:
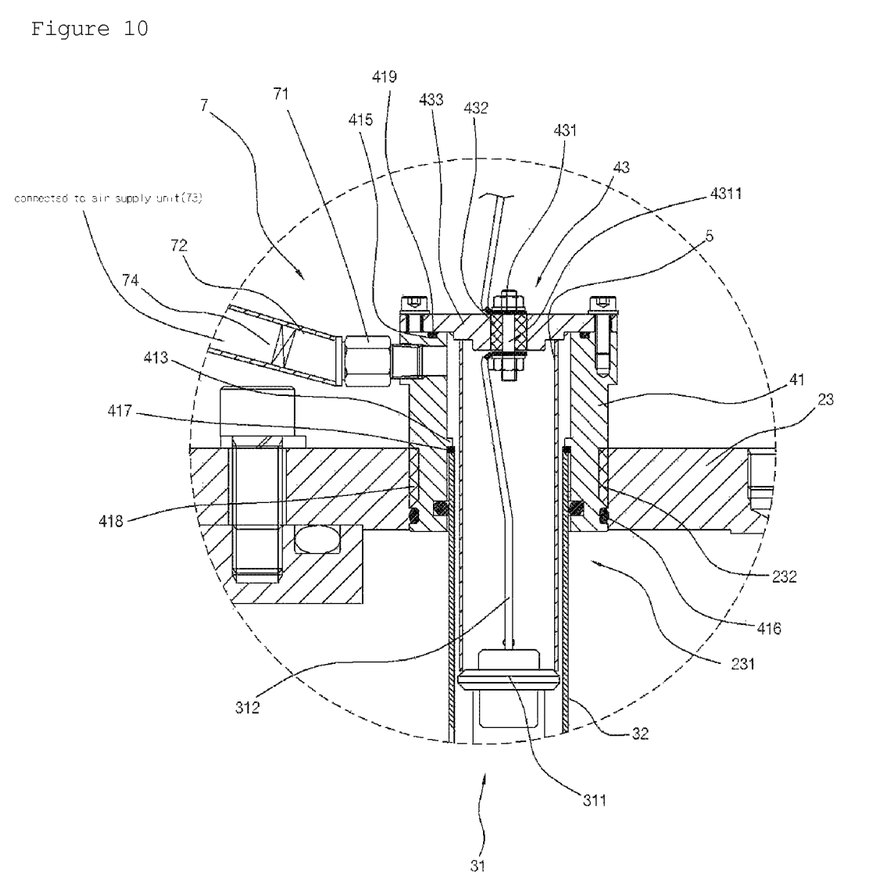
FIG. 10 is an enlarged view showing the circled portion A of FIG. 4 according to a fourth embodiment of the present invention.
Figure 11:
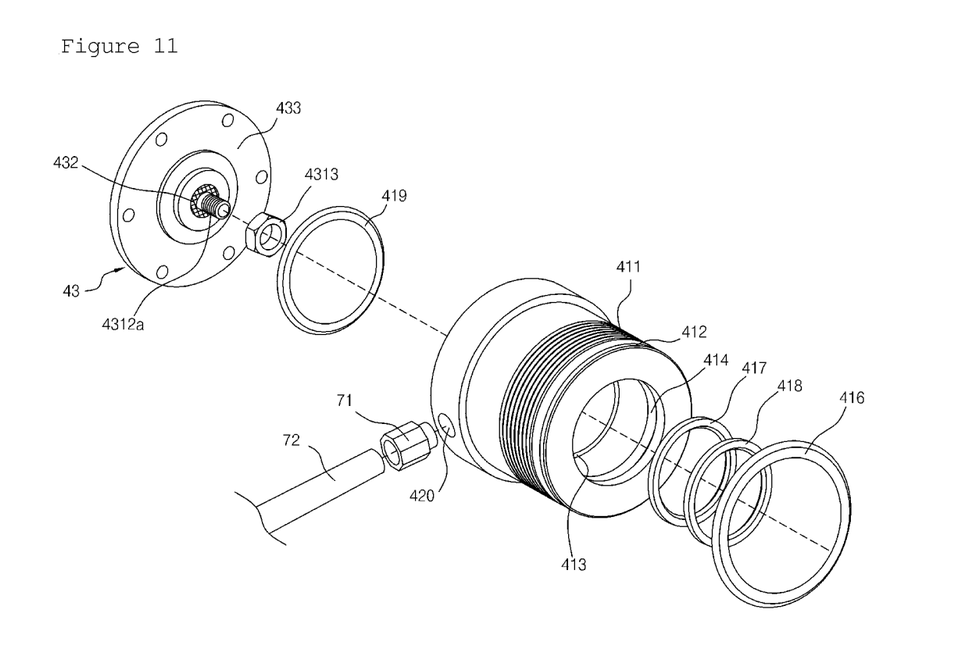
FIG. 11 is an exploded perspective view of a shock absorption unit according to the fourth embodiment of the present invention.
Figure 12:
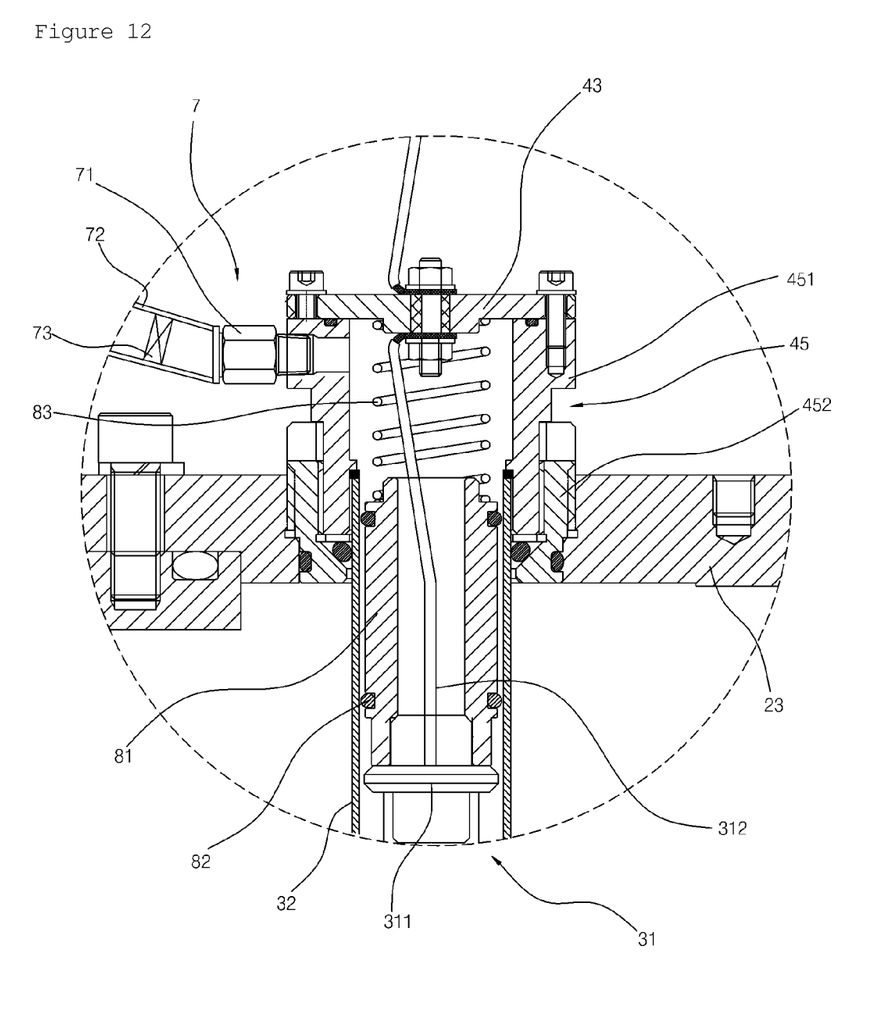
FIG. 12 is an enlarged view showing the circled portion A of FIG. 4 according to a fifth embodiment of the present invention.

FIG. 3 is a partially broken perspective view of an ultraviolet sterilizer, according to a first embodiment of the present invention. FIG. 4 is a sectional view showing the ultraviolet sterilizer according to the first embodiment of the present invention. FIG. 5 is an enlarged view showing the circled portion A of FIG. 4 according to the first embodiment of the present invention. FIG. 6 is an exploded perspective view of a cap according to the first embodiment of the present invention. FIG. 7 is an enlarged view showing the circled portion A of FIG. 4 according to a second embodiment of the present invention. FIG. 8 is an enlarged view showing the circled portion A of FIG. 4 according to a third embodiment of the present invention. FIG. 9 is an exploded perspective view of a shock absorption unit according to the third embodiment of the present invention. FIG. 10 is an enlarged view showing the circled portion A of FIG. 4 according to a fourth embodiment of the present invention. FIG. 11 is an exploded perspective view of a shock absorption unit according to the fourth embodiment of the present invention. FIG. 12 is an enlarged view showing the circled portion A of FIG. 4 according to a fifth embodiment of the present invention.

Referring to FIGS. 3 through 6, the ultraviolet sterilizer having a watertight function according to the first embodiment of the present invention includes a housing 2, an ultraviolet sterilization unit 3, caps 4, supports 5 and a cleaning unit 6.

The housing 2 constitutes the main body of the ultraviolet sterilizer and has a predetermined shape, preferably, a cylindrical shape which is open on the upper and lower ends thereof. Furthermore, the housing 2 has, in a sidewall thereof, an inlet 21 through which ballast water is drawn into the housing 2, and an outlet 22 through which ballast water treated by ultraviolet-sterilizing are discharged from the housing 2. Housing covers 23 are respectively removably coupled to the upper and lower parts of the housing 2 by screwing or the like. The reason that the inlet 21 and the outlet 22 are formed through the sidewalls of the housing 2 is that the efficiency which ballast water passing through the ultraviolet sterilization unit 3 is sterilized can be enhanced.

The housing covers 23 respectively covering the upper and lower parts of the housing 2 are removably coupled to the housing 2 by screwing or the like. Through holes 231 are formed through each housing cover 23 so that the ultraviolet sterilization unit 3 can be inserted into or removed from the housing 2 through the through holes 231 without opening the housing cover 23. The number of through holes 231 corresponds to the number of ultraviolet lamps 31. An internal thread 232 is formed on an inner surface of each through hole 231. Each through hole 231 is covered with the cap 4 which will be explained later herein. The principle of covering the through hole 231 with the cap 4 will be described in detail later.

The ultraviolet sterilization unit 3 applies ultraviolet rays to ballast water that flows through the housing 2 so as to sterilize the ballast water. The ultraviolet sterilization unit 3 includes ultraviolet lamps 31 and sleeve pipes 32.

The ultraviolet lamps 31 are located in the housing 2 and each ultraviolet lamp 31 emits ultraviolet rays and is in the shape of a rod or bar. It is desirable that the ultraviolet lamps 31 be oriented parallel to the axis of the cylindrical housing 2 along the longitudinal direction of the housing 2 and be arranged around the axis housing 2 at positions spaced apart from each other by a regular interval. Thus, ballast water flowing through the inlet 21 and out the outlet 22 passes through space among the ultraviolet lamps 31 in the direction perpendicular to the ultraviolet lamps 31. A head 311 made of material such as a ceramic is coupled to each of both ends of the ultraviolet lamp 31. A lead wire 312 is connected to the ultraviolet lamp 31 by the head 311 so that power is supplied to the ultraviolet lamp 31 through the lead wire 312.

The sleeve pipe 32 encloses the ultraviolet lamp 31 to protect the ultraviolet lamp 31. If impurities are attached to the surface of the sleeve pipe 32, the intensity of ultraviolet rays emitted from the ultraviolet lamp 31 may be reduced. Therefore, the surface of the sleeve pipe 32 is cleaned by the cleaning unit 6 which will be explained later. Preferably, a pipe made of quartz is used as the sleeve pipe 32.

The structure for fastening the sleeve pipes 32 and the ultraviolet lamps 31 in the housing 2 will be explained in detail later herein.

Each cap 4 covers the corresponding through hole 231 and holds one end of the corresponding sleeve pipe 32. The cap 4 includes a cap body 41 and a cap cover 43.

The cap body 41 forms the entire body of the cap 4. The cap body 41 is removably coupled to the corresponding housing cover 23 to cover the corresponding through hole 231. Furthermore, the cap body 41 holds one end of the corresponding sleeve pipe 32. The cap body 41 has a predetermined shape, preferably, a cylindrical shape which is open on the upper and lower ends thereof. The cap body 41 includes an external thread 411, a watertight member insertion groove 412, a stop protrusion 413, a watertight absorber insertion groove 414 and a sealing member insert groove 415.

The external thread 411 is formed around an outer circumferential surface of a lower end of the cap body 41 and corresponds to the internal thread 232 of the through hole 231. Thus, the cap body 41 which has the external thread 411 corresponding to the internal thread 232 of the through hole 231 can be removably coupled to the through hole 231 of the housing cover 23 by threaded coupling.

The watertight member insertion groove 412 is formed around the outer circumferential surface of the cap body 41 below the external thread 411. A watertight member 416 is seated into the watertight member insertion groove 412. The water tight member 416 is located between the inner surface of the through hole 231 and the outer surface of the cap body 41 to ensure watertightness between the through hole 231 and the cap body 41.

The stop protrusion 413 is provided around the inner circumferential surface of the cap body 41 to restrict the sleeve pipe 32 from moving in the longitudinal direction. A shock absorption member 417 is interposed between a lower surface of the stop protrusion 413 and an upper end of the sleeve pipe 32 to absorb longitudinal vibrations of the sleeve pipe 32.

The watertight absorber insertion groove 414 is formed around the inner circumferential surface of the cap body 41 below the stop protrusion 413. A watertight shock-absorber 418 is seated into the watertight absorber insertion groove 414. The watertight shock-absorber 418 is disposed between the inner surface of the cap body 41 and the outer surface of the sleeve pipe 32 to ensure watertightness between the cap body 41 and the sleeve pipe 32 and absorb lateral vibrations of the sleeve pipe 32. Furthermore, the watertight shock-absorber 418 firmly holds the outer surface of the sleeve pipe 32 such that the sleeve pipe 32 is reliably retained in the housing 2.

The sealing member insert groove 415 is formed in an upper surface of the cap body 41 in an annular shape. A sealing member 419 is seated into the sealing member insert groove 415 and located between the upper surface of the cap body 41 and a lower surface of the cap cover 43 to ensure that a watertight seal is formed between the cap body 41 and the cap cover 43.

For example, O-rings can be used as the watertight member 416, the shock absorption member 417, the watertight shock-absorber 418 and the sealing member 419.

The cap cover 43 covers the upper end of the cap body 41 and is removably coupled to the cap body 41 by screwing or the like. The cap cover 43 includes a conductor 431, an insulator 432 and a perimeter part 433.

The conductor 431 is connected to the ultraviolet lamp 31 to supply power to the ultraviolet lamp 31. For example, the conductor 431 is made of conductive material, such as copper or silver. The conductor 431 includes a conductor body 4311 which has a predetermined shape, preferably, a cylindrical shape, and wire connectors 4312 which respectively protrude from upper and lower ends of the conductor body 4311.

In detail, the upper and lower wire connectors 4312 respectively protrude from the upper and lower ends of the conductor body 4311. An external thread 4312a is formed on an outer circumferential surface of each wire connector 4312 so that a nut 4313 is tightened over the wire connector 4312. The lower wire connector 4312 is disposed inside the cap body 41 and connected to the lead wire 312 of the ultraviolet lamp 31. The upper wire connector 4312 is located on the outside of the cap body 41 and connected to a power supply (not shown) which supplies power to the ultraviolet lamp 31. In the embodiment, because the external thread 4312a is formed on the wire connector 4312, the lead wire 311 can be easily connected to the wire connector 4312 by the nut 4313 which is tightened over the wire connector 4312.

The insulator 432 covers an outer circumferential surface of the conductor body 4311. Preferably, the insulator 432 is made of electric insulation material, such as ceramic, synthetic resin, etc. As such, the conductor 431 is covered with the insulator 432, so that high voltage current can be prevented from being applied to portions other than the ultraviolet lamp 31.

The perimeter part 433 encloses the insulator 432 and is coupled to the upper surface of the cap body 41. The perimeter part 433 can be made of various materials including metal.

The conductor 431, the insulator 432 and the perimeter part 433 are tightly integrated with each other such that a gap is prevented from being formed therebetween. For example, the conductor 431 is located inside the annular perimeter part 433 and then a material such as ceramic is deposited on the junction between the perimeter part 433 and the conductor 431, thus preventing a gap from forming therebetween.

In the embodiment, the housing covers 23 are respectively coupled to the upper and lower parts of the housing 2. Thus, the caps 4 are also disposed in the upper and lower parts of the housing 2. Each cap 4 is removably coupled to the corresponding housing cover 23 and divided into the cap body 41 and the cap cover 43. The present invention is not limited to this. For example, a structure in which a cap integrally protrudes from a housing cover must also be regarded as falling within the bounds of the present invention.

Each support 5 is provided in the corresponding sleeve pipe 32 and the corresponding cap 4 between the corresponding end of the ultraviolet lamp 31 and the corresponding cap cover 43. The support 5 functions to support the ultraviolet lamp 31 and has a predetermined shape, preferably, a cylindrical shape which is open on upper and lower ends thereof.

The cleaning unit 6 functions to remove impurities from the surfaces of the sleeve pipes 32. The cleaning unit 6 includes wipers 61, a drive shaft 62 and a drive unit 63. The wipers 61 come into contact with the outer circumferential surfaces of the respective sleeve pipes 32. The drive shaft 62 is coupled to the wiper 61. The drive unit 63 is coupled to the drive shaft to operate the drive shaft.

Each wiper 61 functions to remove impurities from the outer surface of the corresponding sleeve pipe 32 and, preferably, has an annular shape which encloses the entire circumference of the outer surface of the sleeve pipe 32. The wiper 61 is made of synthetic resin or synthetic rubber having heat resistance. The number of wipers 61 corresponds to the number of sleeve pipes 32. In the case where several wipers 61 are used, the wipers 61 are connected to each other by connection arms 611. The connection arms 611 are connected to the drive shaft 62.

The drive shaft 62 is connected to the wipers 61 and operates the wipers 61 to remove impurities from the outer surfaces of the sleeve pipes 32. Preferably, the drive shaft 62 is located in a central portion of the housing 2 and oriented in the direction parallel to the longitudinal axis of the housing 2. An external thread is formed on an outer circumferential surface of the drive shaft 62. One end of the drive shaft 62 is coupled to the drive unit 63.

The drive unit 63 which is coupled to the one end of the drive shaft 62 generates drive force for operating the drive shaft 62 and the wipers 61. A typical motor can be used as the drive unit 63.

Hereinafter, with regard to the ultraviolet sterilizer having the above-mentioned construction, a principle will be described with reference to FIGS. 3 through 6, which can prevent ballast water from being drawn from the housing 2 into a reception space D which contains several devices disposed outside the housing 2 even if the ultraviolet sterilization unit 3 is damaged by impurities or an accident.

The reception space D is formed by the housing cover 23. The reception space D contains therein several devices, for example, the drive unit for operating the cleaning unit, and the power supply for supplying power to the ultraviolet lamps. If ballast water enters the cap 4 owing to damage of the sleeve pipe 32 and then is drawn into the reception space D, the devices in the reception space D may be damaged by the ballast water. However, in the present invention, the cap cover 43 does not require a separate hole through which the lead wire 311 is led out of the cap cover 43. Furthermore, the sealing member 419 is interposed between the upper surface of the cap body 41 and the lower surface of the cap cover 43. Thus, even if the sleeve pipe 32 or the ultraviolet lamp 31 of the ultraviolet sterilization unit 3 is damaged by impurities drawn into the housing 2 or an accident and thus ballast water enters the cap body 41, the ballast water can be prevented from leaking out of the cap body 41, that is, from being drawn into the reception space D. In other words, even if the ultraviolet sterilization unit 3 is damaged, ballast water which has been in the housing 2 enters only the cap 4 without leaking out of the cap 4. Therefore, the devices, such as the drive unit 63 of the cleaning unit 6, etc., can be prevented from being damaged.

The ultraviolet sterilizer according to a second embodiment of the present invention will be described with reference to FIG. 7. The structure of a cap body of the ultraviolet sterilizer according to the second embodiment differs from the ultraviolet sterilizer of the first embodiment which has been explained with reference to FIGS. 3 through 6. Below, the differences in this structure of the cap body from that of the first embodiment will be chiefly described with reference to FIG. 7.

The cap body 45 forms a main body of the cap 4 and includes an upper cap body 451 and a lower cap body 452.

An external thread 4511 is formed around an outer circumferential surface of a lower end of the upper cap body 451. A stop protrusion 4512 is provided around an inner circumferential surface of the upper cap body 451 to restrict the sleeve pipe 32 from moving upwards past the stop protrusion 4512. A sealing member insert groove 4513 is formed in an upper surface of the upper cap body 451. A sealing member 4515 is seated into the sealing member insert groove 4513 to ensure watertightness between the upper cap body 451 and the cap cover 43. A shock absorption member 4514 is interposed between a lower surface of the stop protrusion 4512 and the upper end of the sleeve pipe 32 to absorb longitudinal vibrations of the sleeve pipe 32.

The lower cap body 452 has, around an outer circumferential surface of a lower end thereof, an external thread 4521 corresponding to the internal thread 232 of the through hole 231. A watertight member insertion groove 4522 is formed around the outer circumferential surface of the lower cap body 452 below the external thread 4521. A watertight member 4525 is seated into the watertight member insertion groove 4522 to ensure watertightness between the through hole 231 and the lower cap body 452. A stop protrusion 4523 is provided around an inner circumferential surface of the lower end of the lower cap body 452. A watertight shock-absorber 4526 is interposed between the stop protrusion 4523 and the lower end of the upper cap body 451 to stably support the sleeve pipe 32 and absorb lateral vibrations of the sleeve pipe 32. In addition, the watertight shock-absorber 4526 ensures watertightness among the upper cap body 451, the lower cap body 452 and the sleeve pipe 32. Preferably, each of the watertight member 4525, the shock absorption member 4514, the watertight shock-absorber 4526 and the sealing member 4515 comprises an O-ring.

In the cap body 45 of the ultraviolet sterilizer according to the second embodiment, the upper cap body 451 is removably coupled to the lower cap body 452 by threaded coupling. Thus, only the upper cap body 451 can be separated from the housing 2 so that the through hole 231 can be open while the ultraviolet sterilization unit 3 is still fastened to the housing 2. Therefore, elements of the ultraviolet sterilization unit can be easily replaced with new ones without separating the entirety of the ultraviolet sterilization unit 3 from the housing 2.

Hereinafter, the ultraviolet sterilizer according to a third embodiment of the present invention will be described with reference to FIGS. 8 and 9. The ultraviolet sterilizer of the third embodiment uses a shock absorption unit 8 in place of the support 5 unlike the ultraviolet sterilizer of the first embodiment that was illustrated in FIGS. 3 through 6. Below the structure of the shock absorption unit 8 that differs from that of the first embodiment will be mainly described with reference to FIG. 8.

The shock absorption unit 8 is located in the sleeve pipe 32 and the cap 4 to support the ultraviolet lamp 31 and absorb vibrations. The shock absorption unit 8 includes a support body 81, a shock absorption member 82 and an elastic member 83.

The support body 81 supports the ultraviolet lamp 31 in the sleeve pipe 32. The support body 81 has a predetermined shape, preferably, a hollow cylindrical shape. The support body 81 has a shock absorption member seating groove 811 and a lamp mounting depression 812. The support body 81 can be made of, for example, synthetic resin, such as a Teflon resin, or other insulation material.

The shock absorption member seating groove 811 is formed around an outer circumferential surface of the support body 81. A shock absorption member 82 is seated into the shock absorption member seating groove 811 and disposed between the inner surface of the sleeve pipe 32 and the outer surface of the support body 81. The shock absorption member 82 functions to absorb lateral vibrations of the support body 81. As necessary, the shock absorption member seating groove 811 may comprise a plurality of shock absorption member seating grooves 811.

The lamp mounting depression 812 is formed in an inner circumferential surface of a lower end of the support body 81 at a position corresponding to the head 311 of the ultraviolet lamp 31. The lamp mounting depression 812 receives the ultraviolet lamp 31 such that the ultraviolet lamp 31 is reliably fastened to the support body 81. Preferably, the outermost diameter of the ultraviolet lamp 31 is less than the outer diameter of the support body 81, so that even though the ultraviolet lamp 31 vibrates in the lateral direction, the ultraviolet lamp 31 can be prevented from directly colliding with the sleeve pipe 32.

The shock absorption member 82 is seated into the shock absorption member seating groove 811 such that it is elastically compressed between the inner surface of the sleeve pipe 32 and the outer surface of the support body 81. Thus, the shock absorption member 82 reliably supports the support body 81 on the inner surface of the sleeve pipe 32 and absorbs lateral vibrations of the support body 81. In addition, the support body 81 can be prevented from colliding with the sleeve pipe 32. For example, an O-ring can be used as the shock absorption member 82.

The elastic member 83 is located between an upper end of the support body 81 and the lower surface of the cap cover 43. The elastic member 83 elastically compresses a corresponding end of the support body, thus preventing the support body 81 from vibrating in the longitudinal direction. For example, an elastic spring or the like can be used as the elastic member 83.

Although it is not illustrated in this specification, a structure in which the shock absorption unit 8 of FIGS. 8 and 9 is used in place of the support 5 in the ultraviolet sterilizer of the second embodiment of FIG. 7 must also be regarded as falling within the bounds of the present invention.

Hereinafter, in the ultraviolet sterilizer having the above-mentioned construction, the principle will be described with reference to FIGS. 8 and 9 whereby the ultraviolet sterilization unit 3 can be prevented from being damaged despite a comparatively large impact having been applied to the ultraviolet sterilization unit 3 attributable to water pressure increased by vibrations of the ship or there being a sudden and rapid supply of ballast water.

First, the principle whereby vibrations of the sleeve pipe 32 are absorbed to prevent the sleeve pipe 32 from being damaged will be explained. In the present invention, the watertight shock-absorber 418 is located between the inner surface of the cap body 41 and the outer surface of the sleeve pipe 32. Therefore, even though the sleeve pipe 32 vibrates in the lateral direction, the watertight shock-absorber 418 can absorb the lateral vibrations of the sleeve pipe 32. Furthermore, the shock absorption member 417 is located between the upper end of the sleeve pipe 32 and the lower surface of the stop protrusion 413. Hence, even though the sleeve pipe 32 vibrates in the longitudinal direction, the shock absorption member 417 can absorb the longitudinal vibrations of the sleeve pipe 32. As such, because the watertight shock-absorber 418 or the shock absorption member 417 absorbs the lateral or longitudinal vibrations the sleeve pipe 32, the sleeve pipe 32 can be prevented from directly colliding with the cap 4. Thereby, damage to the sleeve pipe 32 can be prevented.

The principle of absorbing vibrations of the ultraviolet lamp 31 and preventing the sleeve pipe 32 and the ultraviolet lamp 31 from being damaged will be explained. The head of the ultraviolet lamp 31 is inserted into the lamp mounting depression 812 of the support body 81. Thus, the ultraviolet lamp 31 and the support body 81 integrally move. Here, even though the ultraviolet lamp 31 and the support body 81 which are integrated with each other vibrate in the lateral direction, the shock absorption member 82 which is located between the inner surface of the sleeve pipe 32 and the outer surface of the support body 81 can absorb the lateral vibrations of the support body 81 and the ultraviolet lamp 31. Furthermore, even though the ultraviolet lamp 31 and the support body 81 which are integrated with each other vibrate in the longitudinal direction, the elastic member 83 which is disposed between the upper end of the support body 81 and the lower surface of the cap cover 43 can absorb the longitudinal vibrations of the ultraviolet lamp 31 and the support body 81. As such, because the shock absorption member 82 or the elastic member 83 can absorb the lateral or longitudinal vibrations of the ultraviolet lamp 31 and the support body 81, the ultraviolet lamp 31 or the support body 81 can be prevented from directly colliding with the sleeve pipe 32 or the cap 4, thereby preventing damage to the sleeve pipe 32 or the ultraviolet lamp 31.

Hereinafter, the ultraviolet sterilizer according to a fourth embodiment of the present invention will be described with reference to FIGS. 10 and 11. The ultraviolet sterilizer according to the fourth embodiment has the same general construction as that of the ultraviolet sterilizer of the first embodiment of FIGS. 3 through 6 and further includes a pressure controller 7 which is connected to a portion of the cap 4. The pressure controller 7 functions to supply air into the cap 4 such that the internal pressure of the cap 4 is maintained higher than the external pressure.

In this embodiment, an air inlet hole 420 is formed through a portion of the cap body 41.

The pressure controller 7 supplies air into the cap body 41 through the air inlet hole 420 so that the internal pressure of the cap body 41 can be maintained higher than the external pressure. The pressure controller 7 includes a connector 71, an air supply tube 72, an air supply unit 73 and a backflow prevention valve 74.

The connector 71 connects a first end of the air supply tube 72 to the air inlet hole 420. For example, the connector 71 may comprise, for example, a nipple. The first end of the air supply tube 72 is connected to the connector 71, and a second end thereof is connected to the air supply unit 73. For example, a hose made of synthetic resin may be used as the air supply tube 72. The air supply unit 73 is connected to the air supply tube 72 and generates air pressure to supply air into the air supply tube 72. For example, a compressor or the like may be used as the air supply unit 73. The backflow prevention valve 74 is installed at a predetermined position in the air supply tube 72. Even if ballast water is drawn into the cap by a reason of, for example, an accident, the backflow prevention valve 74 can prevent the ballast water from flowing backwards, that is, towards the air supply unit 73.

Several devices or machines are present around the ultraviolet sterilizer which is installed in the ship to treat ballast water. Explosive gas may be present around the ultraviolet sterilizer. If explosive gas enters the cap 4, the ultraviolet sterilizer may explode due to a spark. Therefore, when the internal pressure of the cap body 41 is maintained higher than the external pressure by supplying air from the pressure controller 7 into the cap body 41, even if explosive gas is present around the ultraviolet sterilizer, the explosive gas can be prevented from entering the cap body 41. Therefore, explosive gas can be prevented from exploding the ultraviolet sterilizer.

Meanwhile, a structure in which the pressure controller 7 illustrated in FIGS. 10 and 11 is applied to the ultraviolet sterilizer illustrated in FIGS. 7 through 9 must also be regarded as falling within the bounds of the present invention.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An ultraviolet sterilizer having a watertight function, comprising:
   a housing having an inlet through which ballast water is drawn into the housing, and an outlet through which the ballast water is discharged from the housing after the ballast water has been sterilized;
   an ultraviolet sterilization unit provided in the housing, the ultraviolet sterilization unit comprising an ultraviolet lamp applying ultraviolet rays to the ballast water to sterilize the ballast water;
   a cap supporting an end of the ultraviolet sterilization unit, the cap being watertightly coupled to the housing, wherein the cap has an air inlet hole formed through a predetermined portion of the cap; and
   a pressure controller connected to the predetermined portion of the cap, the pressure controller supplying air into the cap such that an internal pressure of the cap is maintained higher than an external pressure thereof, and the pressure controller includes
      a connector coupled to the air inlet hole,
      an air supply tube connected at a first end thereof to the connector,
      an air supply unit connected to a second end of the air supply tube, the air supply unit generating air pressure to supply air into the air supply tube, and
      a backflow prevention valve provided at a predetermined position in the air supply tube to prevent ballast water from flowing backwards from the cap towards the air supply unit.

* * * * *